(12) United States Patent
Gupta et al.

(10) Patent No.: US 9,008,778 B2
(45) Date of Patent: Apr. 14, 2015

(54) IMPLANTABLE ELECTRICAL STIMULATION SYSTEMS WITH SHIELDED CONTROL MODULE AND METHODS FOR MAKING AND USING

(71) Applicant: Boston Scientific Neuromodulation Corporation, Valencia, CA (US)

(72) Inventors: Gaurav Gupta, Valencia, CA (US); Rafael Carbunaru, Valley Village, CA (US); Kiran Gururaj, Valencia, CA (US); Matthew Lee McDonald, Pasadena, CA (US); Ross Daniel Venook, Millbrae, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/971,262

(22) Filed: Aug. 20, 2013

(65) Prior Publication Data

US 2014/0058482 A1    Feb. 27, 2014

Related U.S. Application Data

(60) Provisional application No. 61/692,632, filed on Aug. 23, 2012.

(51) Int. Cl.
*A61N 1/375* (2006.01)
*A61N 1/36* (2006.01)
*A61N 1/16* (2006.01)

(52) U.S. Cl.
CPC .............. *A61N 1/36142* (2013.01); *A61N 1/16* (2013.01); *A61N 1/3752* (2013.01)

(58) Field of Classification Search
CPC ........... A61N 2001/086; A61N 1/3752; A61N 1/3718
USPC .......................................................... 607/36
See application file for complete search history.

(56) References Cited

U.S. PATENT DOCUMENTS

| 5,131,388 A | 7/1992 | Pless et al. |
| 6,181,969 B1 | 1/2001 | Gord |
| 6,240,317 B1 | 5/2001 | Villaseca et al. |

(Continued)

FOREIGN PATENT DOCUMENTS

WO    WO 2010/126943    * 11/2010    ............... A61N 1/08

OTHER PUBLICATIONS

International Application No. PCT/US2013/055736, International Search Report & Written Opinion mailed Oct. 9, 2013.

(Continued)

*Primary Examiner* — Michael Kahelin
(74) *Attorney, Agent, or Firm* — Lowe Graham Jones PLLC; Bruce E. Black

(57) ABSTRACT

An implantable control module for an electrical stimulation system includes a header coupled a sealed body. The header includes at least one connector assembly. The control module also includes a conductive shield disposed over at least a portion of the connector assembly or connector assemblies of the header. The conductive shield is provided to hinder generation of current in the header or in a portion of a lead received in the header in response to application of an external radiofrequency (RF) or magnetic field. A similar shield can also be used to shield a connector assembly disposed on the end of a lead extension or any other component of the electrical stimulation system.

12 Claims, 14 Drawing Sheets

(56) References Cited

U.S. PATENT DOCUMENTS

| | | |
|---|---|---|
| 6,510,345 B1 | 1/2003 | Van Bentem |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,620,453 B1 * | 11/2009 | Propato et al. ............ 607/37 |
| 7,672,734 B2 | 3/2010 | Anderson et al. |
| 7,761,165 B1 | 7/2010 | He et al. |
| 7,822,484 B1 | 10/2010 | Zhao et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 2005/0222633 A1 * | 10/2005 | Edvardsson ............ 607/36 |
| 2007/0150036 A1 | 6/2007 | Anderson |
| 2008/0039898 A1 | 2/2008 | Lim et al. |
| 2008/0051854 A1 | 2/2008 | Bulkes et al. |
| 2009/0149906 A1 | 6/2009 | Ameri et al. |
| 2011/0112612 A1 | 5/2011 | Rahman |
| 2011/0137414 A1 | 6/2011 | Litzke et al. |
| 2012/0123500 A1 * | 5/2012 | Erickson ............ 607/45 |
| 2012/0191167 A1 | 7/2012 | McDonald et al. |
| 2012/0221074 A1 | 8/2012 | Brase et al. |

OTHER PUBLICATIONS

U.S. Appl. No. 14/475,235, filed Sep. 2, 2014.

* cited by examiner

IMPLANTABLE ELECTRICAL STIMULATION SYSTEMS WITH SHIELDED CONTROL MODULE AND METHODS FOR MAKING AND USING

CROSS-REFERENCE TO RELATED APPLICATIONS

This application claims the benefit under 35 U.S.C. §119 (e) of U.S. Provisional Patent Application Ser. No. 61/692,632 filed on Aug. 23, 2012, which is incorporated herein by reference.

FIELD

The present invention is directed to the area of implantable electrical stimulation systems and methods of making and using the systems. The present invention is also directed to implantable electrical stimulation leads having a shield on or within the header of a control module, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat incontinence, as well as a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

One embodiment is an implantable control module for an electrical stimulation system. The control module includes a sealed body; an electronic subassembly disposed in the sealed body and configured and arranged to generate to generate electrical stimulation signals for delivery through a lead coupled to the implantable control module; and a header coupled the sealed body. The header includes at least one connector assembly. Each connector assembly defines a port with each connector assembly configured and arranged to receive a proximal portion of a lead inserted into the port. The header also includes a plurality of contacts disposed within each connector assembly and configured and arranged to make contact with terminals disposed on a lead when the lead and terminals are received in the connector assembly and to electrically couple the terminals of the lead to the electronic subassembly. The control module also includes a conductive shield disposed over at least a portion of the at least one connector assembly of the header. The conductive shield is configured and arranged to hinder generation of current in the header or in a portion of a lead received in the header in response to application of an external radiofrequency (RF) or magnetic field.

Another embodiment is an implantable lead extension for an electrical stimulation system. The lead extension includes an extension body having a proximal end, a distal end, and a longitudinal length; a plurality of conductive contacts disposed along the proximal end of the extension body; and a connector assembly disposed on the distal end of the extension body. The connector assembly defines at least one port configured and arranged to receive a proximal portion of a lead inserted into the port. The connector assembly also includes a plurality of contacts disposed within the connector assembly and configured and arranged to make contact with terminals disposed on a lead when the lead and terminals are received in the connector assembly. The lead extension further includes a plurality of conductive wires electrically coupling the conductive contacts along the proximal end of the extension body to the contacts of connector assembly; and a conductive shield disposed over at least a portion of the connector assembly. The conductive shield is configured and arranged to hinder generation of current in the connector assembly or in a portion of a lead received in the connector assembly in response to application of an external radiofrequency (RF) or magnetic field.

Other embodiments include an electrical stimulation system including at least one lead and either the control module or the extension lead, or both, described above.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having a shield on or within the header of a control module, as well as methods of making and using the leads and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; 8,224,450; and 8,364,278; and U.S. Patent Application Publication No. 2007/0150036, all of which are incorporated by reference.

Figure 1:
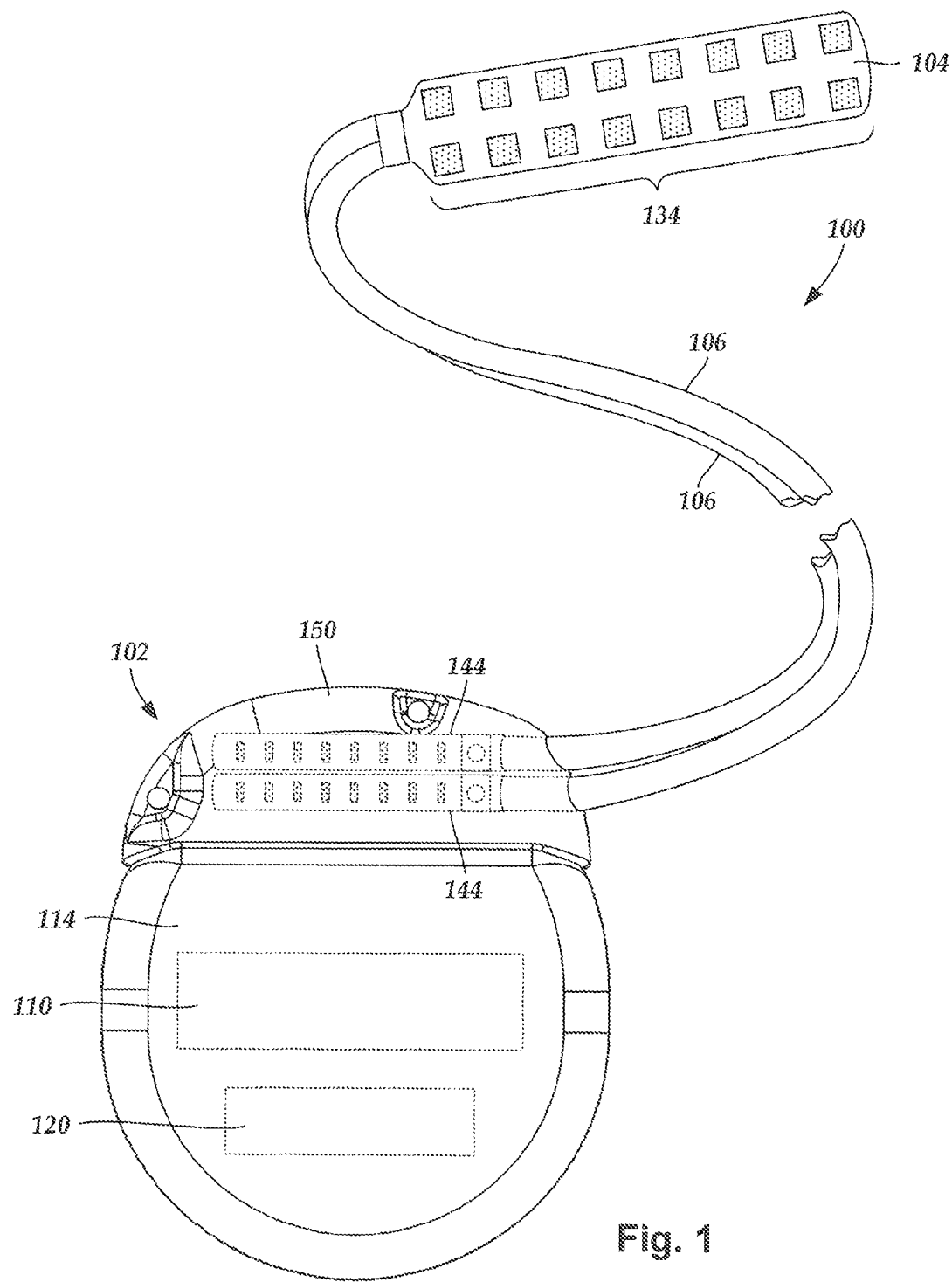
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed body 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIGS. 3A-3B; and 340 of FIG. 3C) disposed in the connector assembly 144 and terminals (e.g., 310 in FIGS. 3A-3C) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
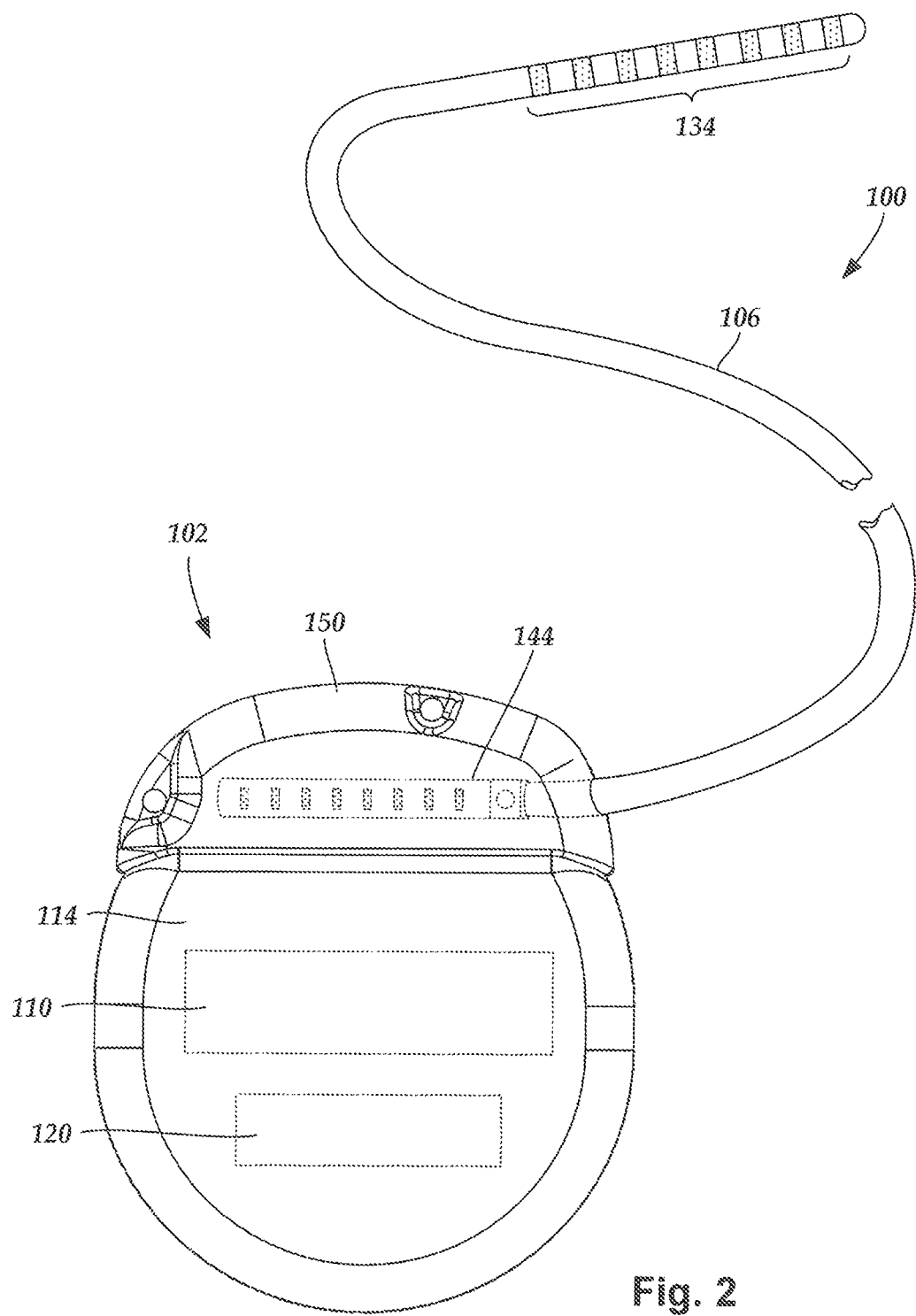
FIG. 2 is a schematic view of another embodiment of an electrical stimulation system that includes a percutaneous lead body coupled to a control module via a lead body, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead body 106.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle stimulation, cardiac stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 134 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIGS. 3A-3C) are typically disposed at the proximal end of the one or more lead bodies 106 for connection to corresponding conductive contacts (e.g., 316 in FIGS. 3A-3B; and 340 of FIG. 3C) in connector assemblies (e.g., 144 in FIGS. 1-3C) disposed on, for example, the control module 102 (or to other devices, such as conductive contacts on a lead extension, an operating room cable, a splitter, an adaptor, or the like).

Conductive wires (not shown) extend from the terminals (e.g., 310 in FIGS. 3A-3C) to the electrodes 134. Typically, one or more electrodes 134 are electrically coupled to a terminal (e.g., 310 in FIGS. 3A-3C). In some embodiments, each terminal (e.g., 310 in FIGS. 3A-3C) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
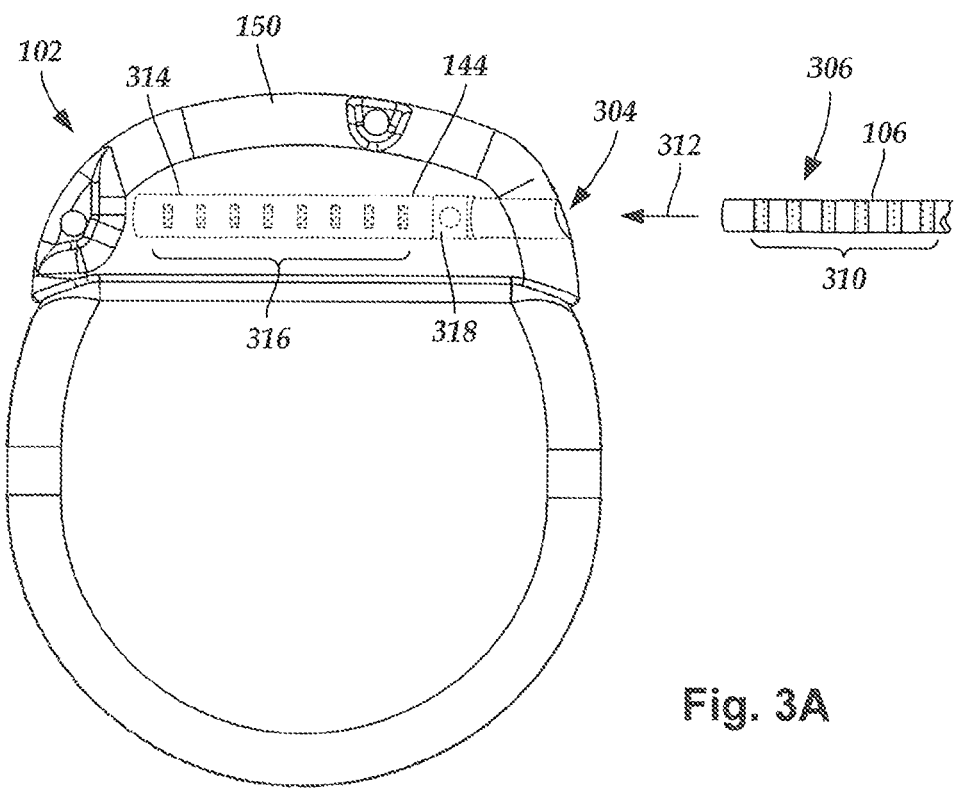
FIG. 3A is a schematic view of one embodiment of a plurality of connector assemblies disposed in the control module of FIG. 1, the connector assemblies configured and arranged to receive the proximal portions of the lead bodies of FIG. 1, according to the invention.
Figure 3B:
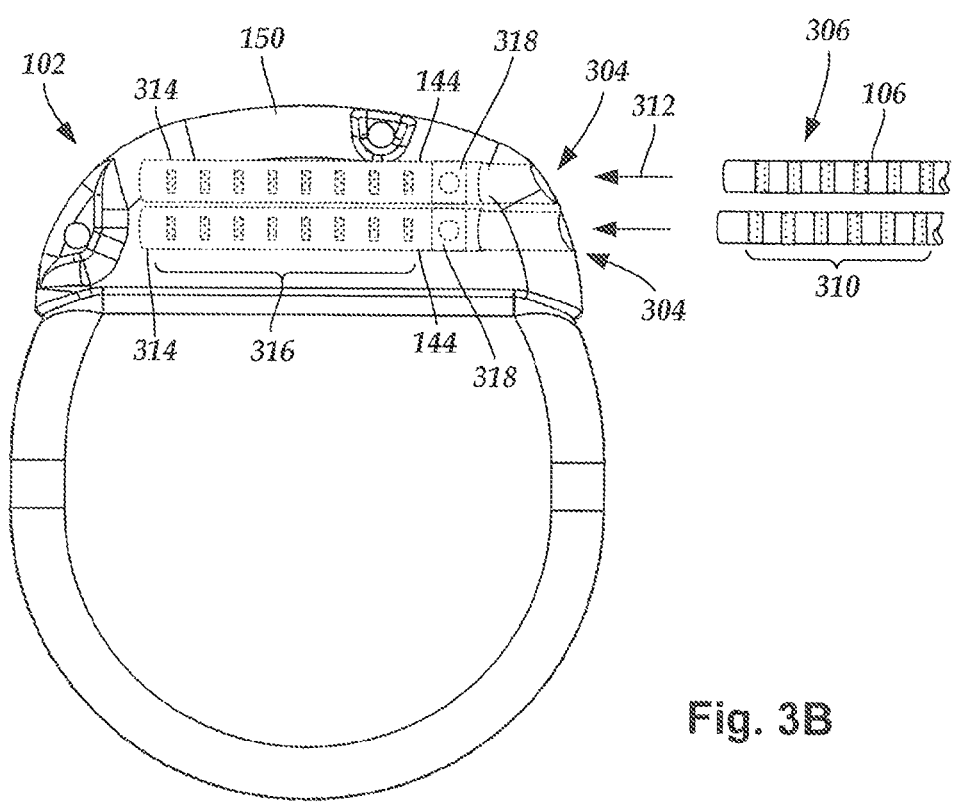
FIG. 3B is a schematic view of one embodiment of a connector assembly disposed in the control module of FIG. 2, the connector assembly configured and arranged to receive the proximal portion of one of the lead body of FIG. 2, according to the invention.

In at least some embodiments, leads are coupled to connectors disposed on control modules. FIG. 3A is a schematic perspective view of one embodiment of a single connector assembly 144 disposed on the control module 102. FIG. 3B is a schematic perspective view of one embodiment of a plurality of connector assemblies 144 disposed on the control module 102. In at least some embodiments, the control module 102 includes two connector assemblies 144. In at least some embodiments, the control module 102 includes four connector assemblies 144.

In FIGS. 3A and 3B, the proximal ends 306 of one or more lead bodies 106 are shown configured and arranged for insertion to the control module 102. In FIGS. 3A and 3B, the one or more connector assemblies 144 are disposed in the header 150. In at least some embodiments, the header 150 defines one or more ports 304 into which a proximal end 306 of the one or more lead bodies 106 with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 308 to the connector assembly 144 when the lead body 106 is inserted into the connector assembly 144 to prevent undesired detachment of the lead body 106 from the connector assembly 144. For example, the retaining element 318 may include an aperture through which a fastener (e.g., a set screw, pin, or the like) may be inserted and secured against an inserted lead body or lead extension.

When the one or more lead bodies 106 are inserted into the one or more ports 304, the connector contacts 316 can be aligned with the terminals 310 disposed on the one or more lead bodies 106 to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference.

Figure 3C:
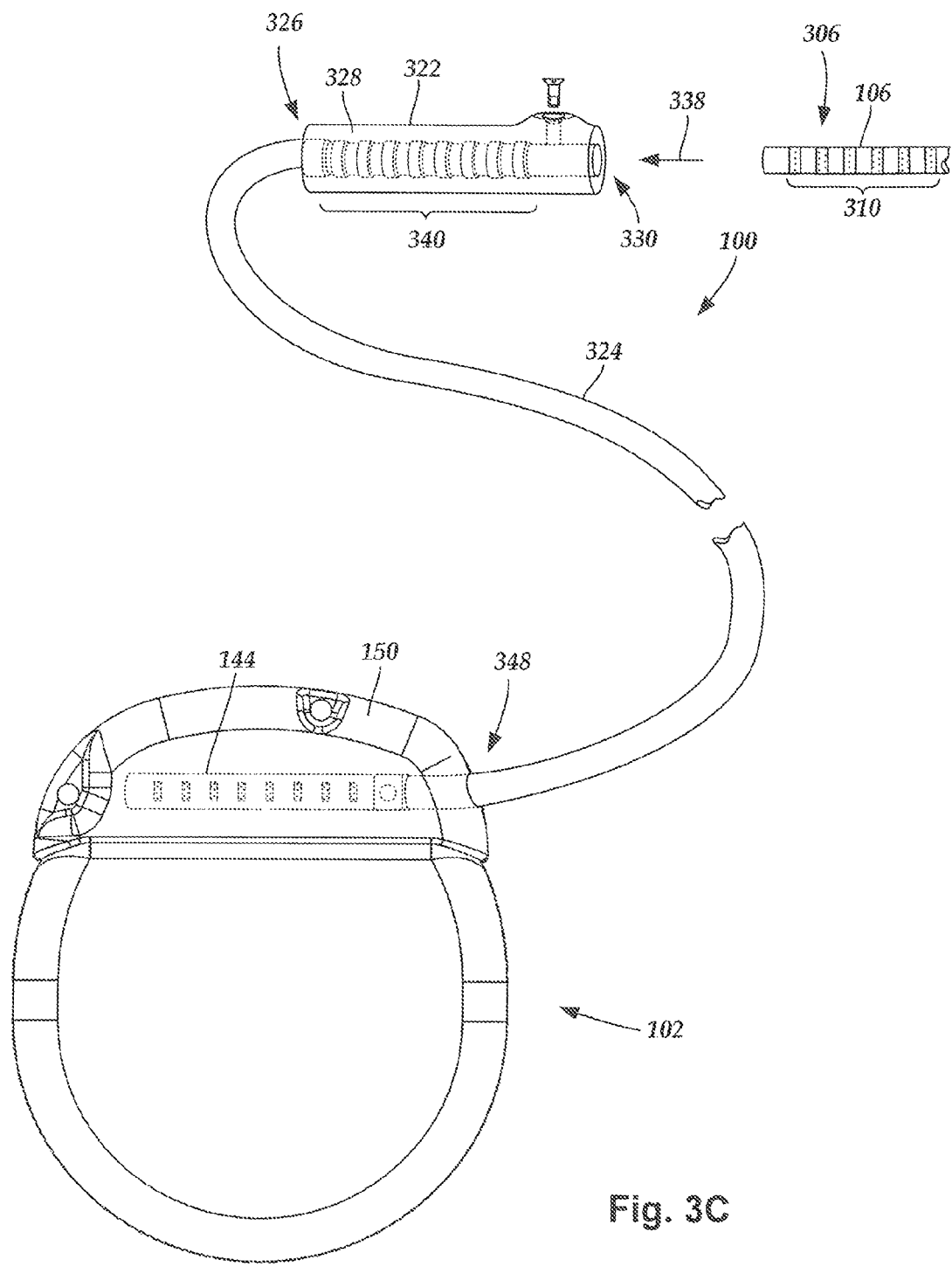
FIG. 3C is a schematic view of one embodiment of a proximal portion of the lead body of FIG. 2, a lead extension, and the control module of FIG. 2, the lead extension configured and arranged to couple the lead body to the control module, according to the invention.

In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106 with terminals 310 can be inserted, as shown by directional arrow 338. The lead extension connector assembly 322 also includes a plurality of connector contacts 340. When the lead body 106 is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106.

The proximal end of a lead extension can be similarly configured and arranged as a proximal end of a lead body. The lead extension 324 may include a plurality of conductive wires (not shown) that electrically couple the connector contacts 340 to a proximal end 348 of the lead extension 324 that is opposite to the distal end 326. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102.

Conventional electrical stimulation systems may be potentially unsafe for use with magnetic resonance imaging ("MRI") due to the effects of electromagnetic fields (e.g., radiofrequency fields and magnetic field gradients) in an MRI environment. A common mechanism for causing the electrical interactions between the electrical stimulation system and radiofrequency ("RF") irradiation is common-mode coupling of the applied electromagnetic fields that act as a series of distributed sources along elongated conductive structures, such as leads, or conductors within leads. Common-mode induced RF currents can reach amplitudes of greater than one ampere in MRI environments. Such currents can cause heating and potentially disruptive voltages within electronic circuits, such as electronic circuits disposed within the electronic subassembly.

Some of the effects of RF irradiation may include, for example, inducing current in the lead, causing undesired heating around the lead that may potentially cause tissue damage, undesired or unexpected operation of electronic components, or damage to, or premature failure of, electronic components. Additionally, when an electrical stimulation system is used within an MRI scanner environment, the electrical interactions between the electrical stimulation system and the MRI may cause distortions in images formed by the MRI system.

When the lead is exposed to electromagnetic fields, RF energy may be induced along the length of the lead. It has been found that in many instances a major portion of the RF energy induced in the lead occurs in the distal and proximal ends of the lead. When the lead is coupled to the control module, at least some of the RF energy induced along the lead may propagate from the lead to the control module. The RF energy may, for example, propagate between the terminals of the lead and the connector contacts of the connector assembly of the control module. Once the induced RF energy reaches the control module, the RF energy may propagate along a plurality of different conductive paths to the electronic subassembly.

In addition, it has been found that local heating may occur in tissue near the junction between the header 150 and sealed body 114 of the control module 102 (see, FIG. 2), particularly when the exterior of the sealed body is made of metal (e.g., titanium) or metalized and the header 150 is made of a non-conductive material (e.g., medical grade epoxy or polyurethane). It is believed that the discontinuity in the dielectric constant and conductivity between the tissue and the header may cause electromagnetic fields and currents to build up especially near the header-tissue-sealed body interface and cause local heating (e.g., "hotspots") in the adjacent tissue.

Shielding of at least a portion of the header of the control module can reduce the current induced in attached leads and delivered to the control module. It is also believed that the shielding may reduce or eliminate the dielectric discontinuity between the header and the tissue resulting in lower or more homogenous tissue heating.

Figure 4:
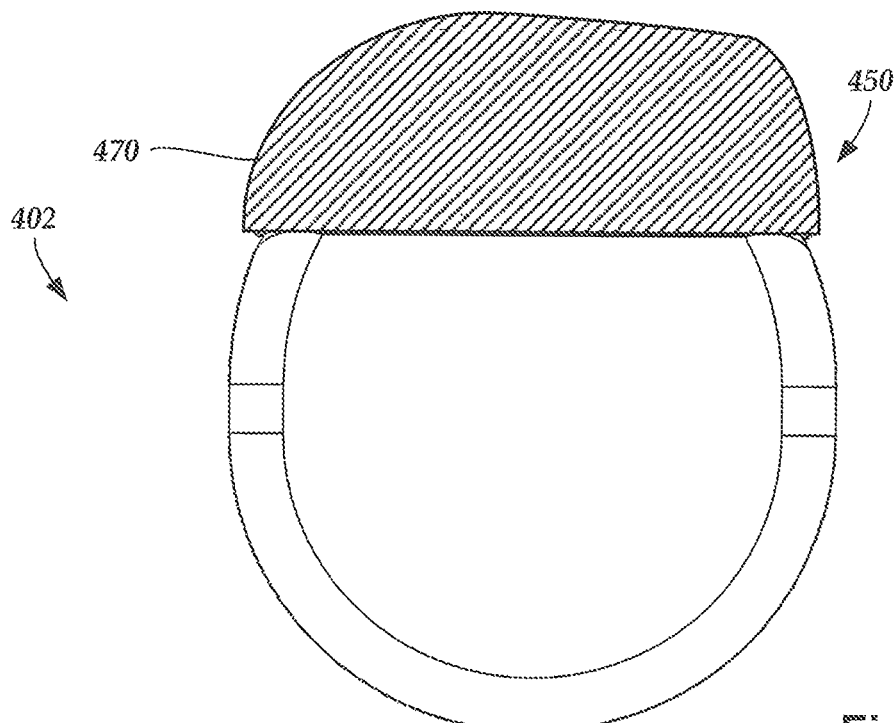
FIG. 4 is a schematic side view of one embodiment of a control module with a shield disposed over the header, according to the invention.

A variety of different shield arrangements can be used. FIG. 4 illustrates one arrangement with a metal shield 470 disposed over at least a portion of the header 450 of the control module 402. The shield 470 does not extend over the ports 304 (FIG. 3A) that receive the leads (or lead extensions). The shield 470 can be made of any suitable biocompatible material such as metals or alloys, including, but not limited to, copper, stainless steel, titanium, and the like. The shield 470 may take the form of, for example, a solid sheet or foil of material, a mesh, or a layer of conductive material formed (for example, by physical or chemical deposition) on the control module or on a substrate (for example, a polymeric substrate) disposed on the header, or any combination thereof.

In at least some embodiments, the shield 470 may be removable from the control module 402. In at least some embodiments, the shield 470 may be permanently or temporarily affixed to the control module 402. Affixation can be accomplished using, for example, adhesive, soldering, welding, brazing, press fitting, or any other suitable affixation method or medium.

In at least some embodiments, the shield 470 may be attached to the control module 402 as part of the manufacture of the control module. In some embodiments, the shield may be attached or otherwise coupled to the control module after manufacture of the control module. In some embodiments, a shield may be arranged to retrofit an existing control module or as an optional component for the control module.

In at least some embodiments, the shield 470 (or any of the other shields described herein) may be coupled to the electronic subassembly 110 (FIG. 1) of the control module 402 (for example, coupled to interconnects that extend between the header and the sealed body) so that the shield 470 can act as a return electrode in combination with one or more of the electrodes on the lead. The sealed body 114 (FIG. 1) of the control module may be non-conductive.

Figure 5A:
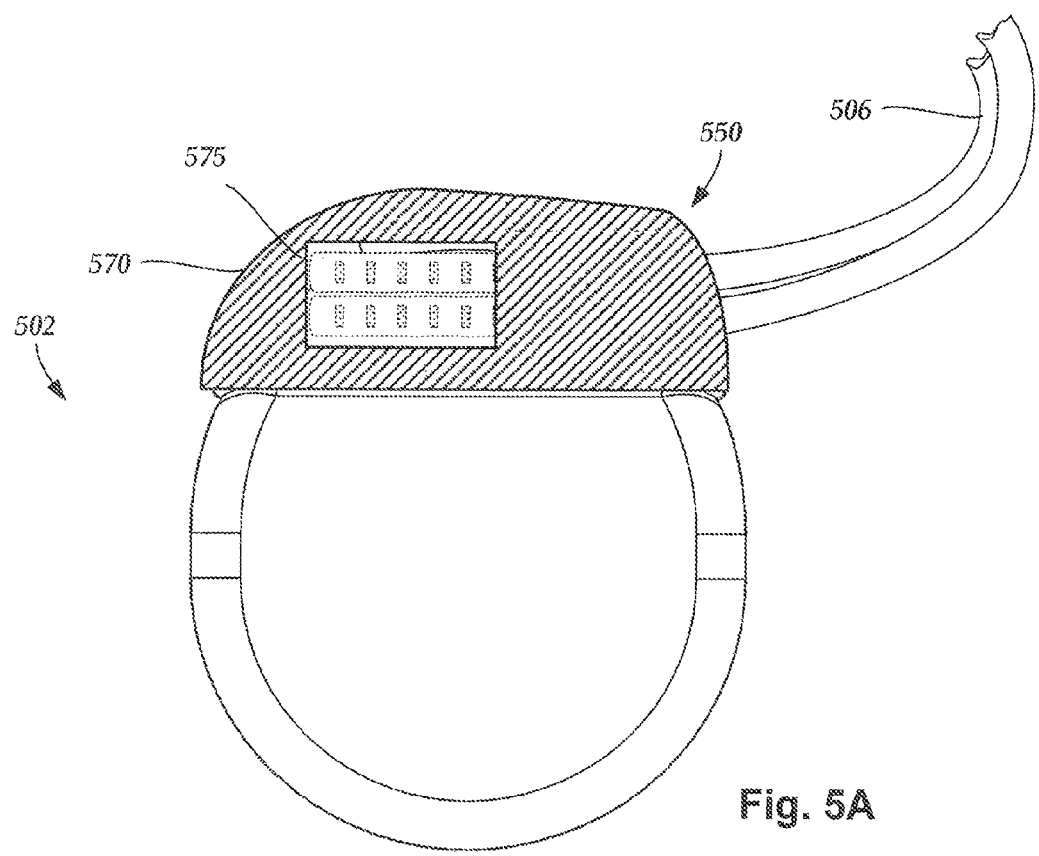
FIG. 5A is a schematic side view of one embodiment of a control module with a shield disposed over the header, where the shield defines a window surrounded on all sides of its perimeter by the shield, according to the invention.

In at least some embodiments, the shield may include a window to allow a practitioner to view a portion of the lead(s) inserted into the header to verify insertion or alignment of the lead(s) within the control module using visual or imaging (e.g., x-ray imaging) techniques. FIG. 5A illustrates one embodiment of a shield 570 with at least one window 575 and disposed on a header 550 of a control module 502. The proximal ends of the leads 506 are visible through the window 575, as are the conductive contacts 516 of the header 550. A window 575 may be provided on only one side of the shield 570 or on both opposing sides of the shield. The window 575 may have any suitable regular or irregular shape including, but not limited to, square, rectangular, circular, oval, triangular, and the like. In this embodiment, the perimeter of the window 575 is defined on all sides by the shield 570.

Figure 5B:
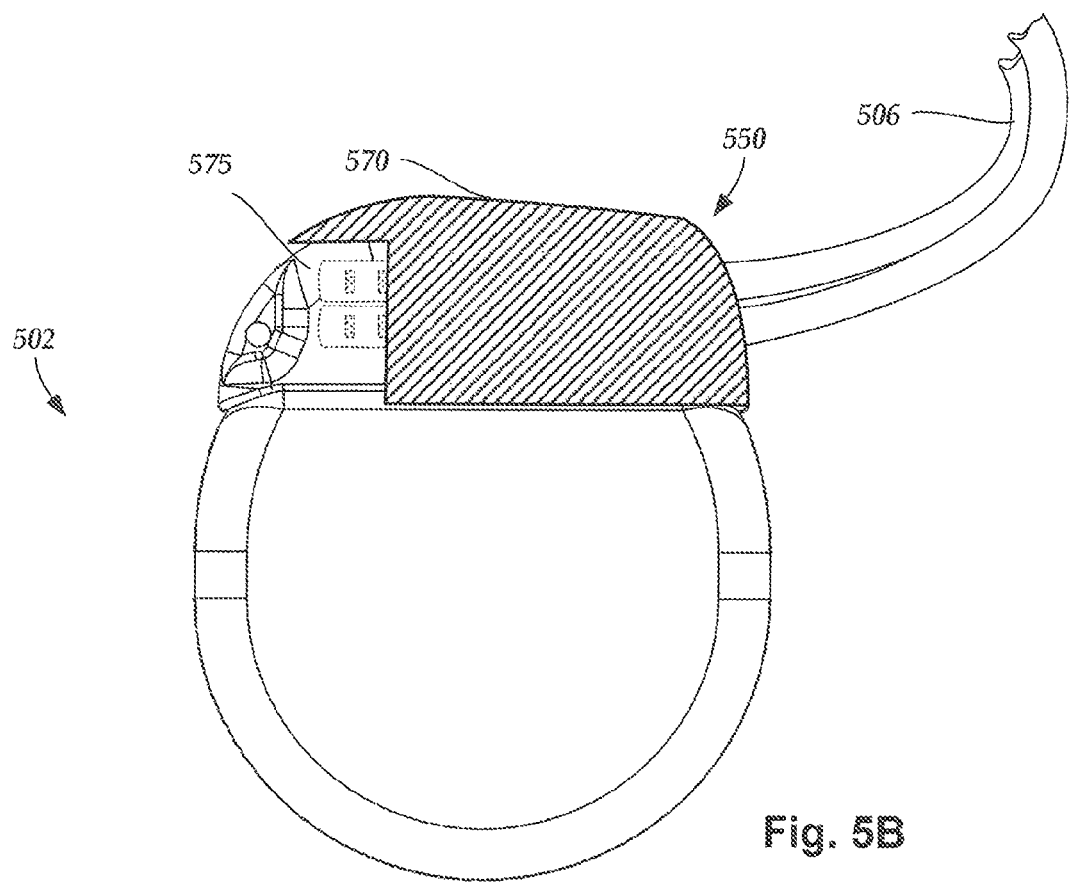
FIG. 5B is a schematic side view of one embodiment of a control module with a shield disposed over the header, where the shield defines a window surrounded on only some of the sides of its perimeter by the shield, according to the invention.

FIG. 5B illustrates another embodiment of a shield 570 with at least one window 575 and disposed on a header 550 of a control module 502. In this embodiment, the window 575 can be a cutout portion of the shield 570 where less than the entire perimeter of the window 575 is surrounded by the shield 570. It will be understood that, despite being described as a "cutout", the window 575 is not necessarily cut out of the shield, but that the shield may be initially formed with the window. In this context, the term "window" is used to indicate that the shield 570 does not cover the entire header, but rather leaves a portion of the header uncovered so that the practitioner can observe a portion of the lead(s) through the window.

It will be recognized that a shield may include more than one window. It will also be recognized that a window in the shield may be provided for some purpose other than observation of the lead(s) inserted into the header of the control module. It will also be recognized that one or more windows may be incorporated in any of the other embodiments of a shield discussed below.

Figure 6:
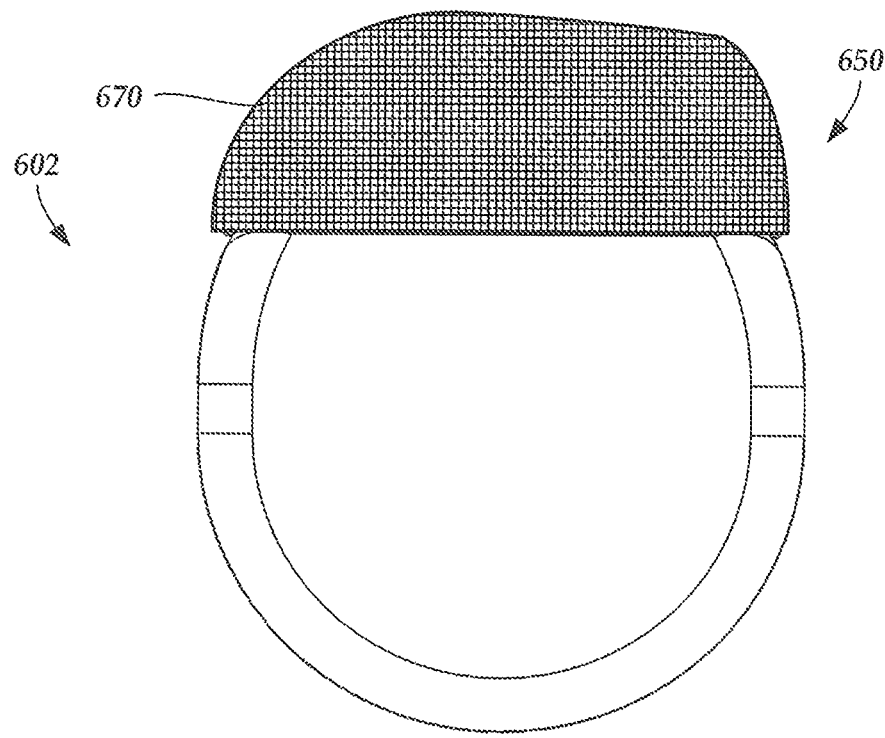
FIG. 6 is a schematic side view of one embodiment of a control module with a shield disposed over the header, where the shield has a frequency selective surface, according to the invention.

In another embodiment, illustrated in FIG. 6, a shield 670 is formed on, or disposed over, the header 650 of a control module 602. The shield 670 includes a surface that is structured as a frequency selective surface. Frequency selective surfaces, and methods of making such surfaces, are known. At least some embodiments of a frequency selective surface include two-dimensional periodic arrays of metallic elements with specific geometric shapes or arrangements (or both) formed on a substrate (such as a polymeric substrate or the surface of the header 650). In other embodiments, the frequency selective surface is a two-dimensional array of apertures in a metallic sheet or foil with the apertures having specific geometric shapes or arrangements (or both).

The period and shape (or other parameters, such as thickness) of the metallic elements or apertures can be selected and tuned to a particular frequency or to two or more frequencies or to one or more bands of frequencies. For example, a shield 670 may have a frequency selective surface that is tuned to one or more expected RF frequencies used in MRI procedures such as, for example, 64 MHz or 128 MHz (or both) to attenuate transmission of the electromagnetic energy at the tuned frequency or frequencies into the header. Electromagnetic energy at other frequencies will be less attenuated by the shield or not attenuated at all.

Such a shield 670 may be desirable as, at least in some embodiments, it allows low frequency signals, such as telemetry signals which may be used to operate, reprogram, or otherwise communicate with the control module, to be received by the control module while at least partially shielding from RF frequencies used in MRI procedures.

In at least some embodiments, the frequency selective surface may be formed directly on the header of the control module, for example, as a patterned layer formed on the control module using deposition and photolithographic or other patterning techniques. In at least some embodiments, the frequency selective surface may be formed on a substrate, such as a polymer substrate, which is then placed over at least a portion of the header of the control module.

Figure 7:
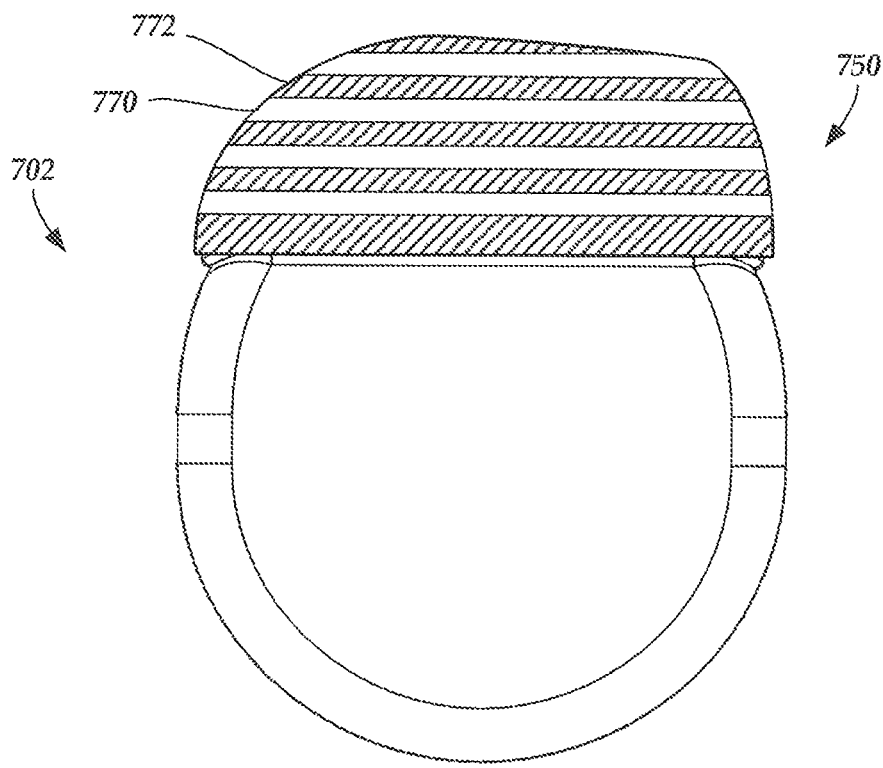
FIG. 7 is a schematic side view of one embodiment of a control module with a patterned shield disposed over the header, according to the invention.

Other patterned shields can be useful. For example, a shield may include a series of slats, stripes or other thin structures to shield electromagnetic fields that are not parallel to these structures. FIG. 7 illustrates one embodiment of a shield 770 disposed on a header 750 of a control module 702. The shield 770 includes multiple elongated conductive structures 772, such as slats or stripes. In at least some embodiments, these elongate conductive structures 772 are arranged to extend parallel one or more lead(s) inserted in the control module 702. The width, thickness, material, or other parameters of the elongated structures may be uniform or non-uniform.

The width, thickness, material, or other parameters of the elongated structures, or any combination thereof, may be selected to facilitate shielding of electromagnetic radiation having a particular orientation or polarization (e.g., polarized perpendicular to the elongated structures) or orientations or a particular frequency or frequencies. It will be understood that, in at least some embodiments, the shield 770 may preferentially reflect or absorb one polarization of electromagnetic radiation and preferentially transmit another polarization of the electromagnetic radiation.

In at least some embodiments, the elongated structures 772 may be formed directly on the header 750 of the control module 770, for example, as a patterned layer formed on the control module using deposition and photolithographic or other patterning techniques. In at least some embodiments, the elongated structures 772 may be formed on a substrate, such as a polymer substrate, which is then placed over at least a portion of the header of the control module.

Figure 8:
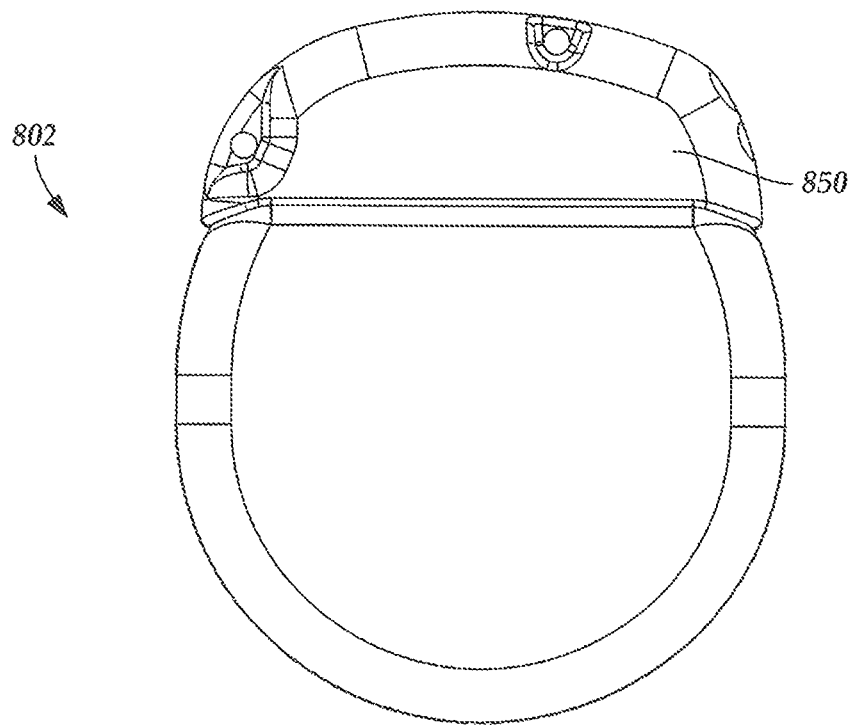
FIG. 8 is a schematic side view of one embodiment of a control module with a shield formed by doping or impregnating plastic material of the header with a conductive material, according to the invention.

In another embodiment, the plastic material of the header, or a portion of the plastic material of the header, includes a doping or impregnating conductive material that renders that plastic material conductive and able to shield RF energy. FIG. 8 illustrates one embodiment of a header 850 of a control module 802 where the header includes a plastic material that is doped or impregnated with a conductive material to render the plastic material conductive to shield from RF energy. Examples of suitable conductive material for doping or impregnating the plastic material include, but are not limited to, metal or alloy particles or conductive carbon particles or conductive polymers. The plastic material can be any suitable plastic material such as, for example, silicone, polyurethane, or polyetheretherketone. The doped or impregnated plastic material preferably extends through at least the portion of the header surrounding the conductive assembly or conductive assemblies 144 (FIG. 1) into which the lead(s) are to be inserted. Preferably, the doped or impregnated plastic material does not conductively couple to any of the contacts within the conductive assembly otherwise it may short the contacts and affect stimulation signal delivery.

In any of the embodiments described herein, a shield disposed on or in the header may be electrically coupled to a conductive structure, such as an electrode, disposed, or otherwise formed, on the surface of the body of the control module. In at least some embodiments, this conductive structure is an electrode that is coupled to the electronic subassembly 110 (FIG. 1) disposed within the body of the control module. This electrode may, for example, act as a return electrode in conjunction with one or more electrodes on the leads 106 (FIG. 1).

Figure 9:
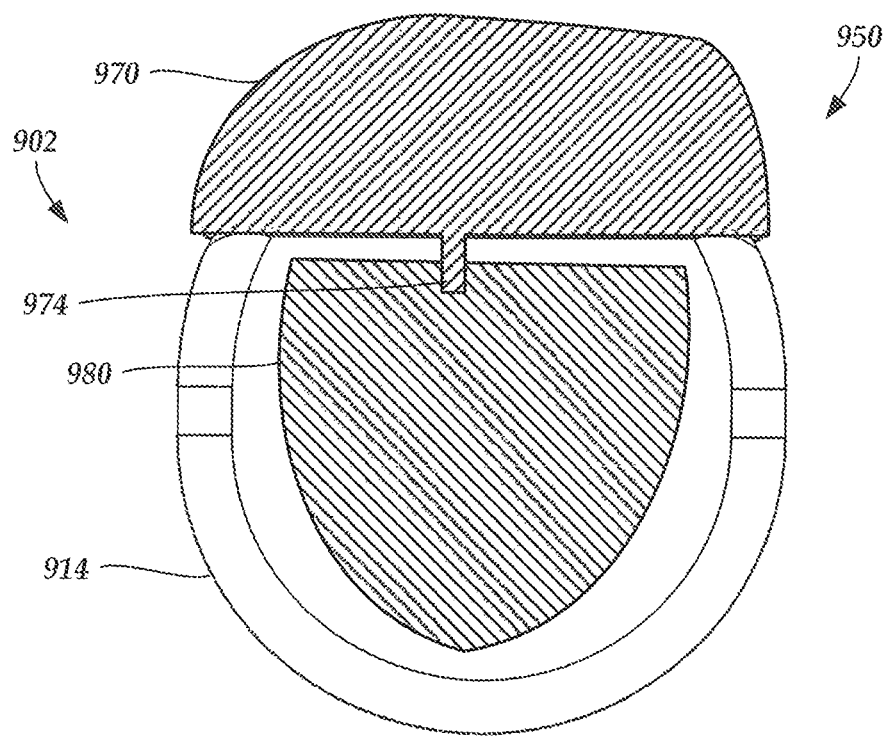
FIG. 9 is a schematic side view of one embodiment of a control module with a shield disposed over the header and conductively coupled to a conductive structure disposed on the body of the control module, according to the invention.

FIG. 9 illustrates one embodiment of a shield 970, disposed on a header 950 of a control module 902, that is electrically coupled to a conductive structure 980 disposed on the body 914 of the control module. In the illustrated embodiment of FIG. 9, a conductive element 974 conductively couples the shield 970 to the conductive structure 980.

In at least some embodiments, the conductive structure 980 is a case of the body 914 of the control module 902 and extends around the entire body of the control module. In other embodiments, the conductive structure 980 is formed only on a portion of the surface of the body 914 of the control module 902.

Although FIG. 9 illustrates contact between the shield and conductive structure at a single point 974, it will be understood that contact between the shield and conductive structure can be made at multiple points or over one or more elongated regions. In at least one embodiment, contact between the shield and the conductive structure on the body of the control module can be made circumferentially around the entire circumference of the control module (assuming that both the shield and conductive structure extend circumferentially around the entire circumference of the control module) or around at least 50%, 60%, 70%, 75%, 80%, 90%, or more of the circumference of the control module.

Figures 10A, 10B:
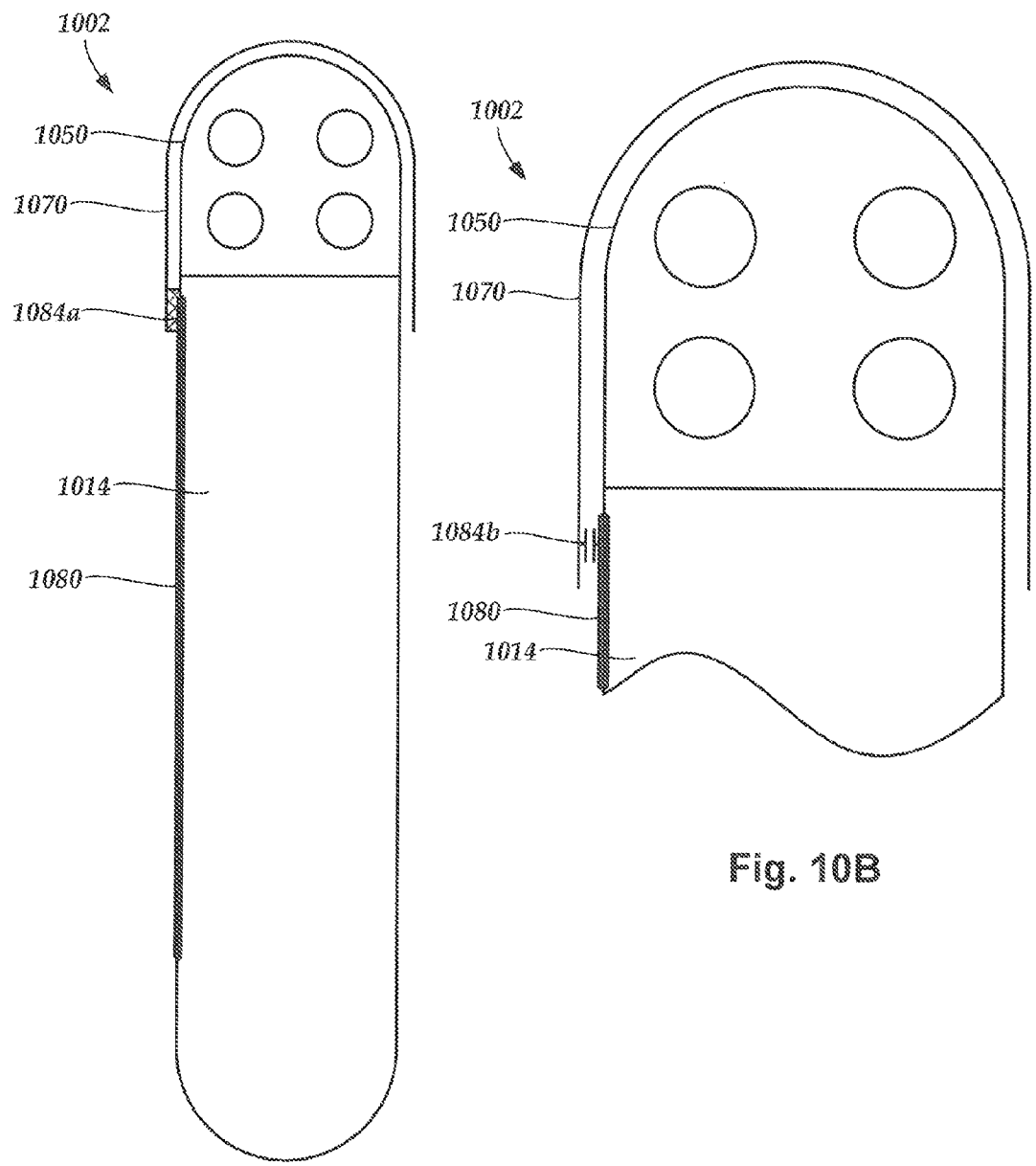
FIG. 10A is a schematic front view of the lead-receiving side of one embodiment of a control module with a shield disposed over the header and capacitively coupled via a solid dielectric material to a conductive structure disposed on the body of the control module, according to the invention.
FIG. 10B is a schematic front view of a portion of the lead-receiving side of one embodiment of a control module with a shield disposed over the header and capacitively coupled via a discrete capacitor to a conductive structure disposed on the body of the control module, according to the invention.

Alternatively, the shield can be capacitively, instead of conductively, coupled to the conductive structure on the body of the control module. FIG. 10A illustrates one embodiment of a shield 1070 that is disposed over a header 1050 of a control module 1002. The body 1014 of the control module includes a conductive structure 1080, such as an electrode. A solid dielectric material 1084a is disposed between the shield 1070 and the conductive structure 1080 so that the shield and conductive structure are capacitively coupled. Any of the specific type of material, size, shape, thickness, and dielectric constant of the solid dielectric material, as well as the separation distance and extent of overlap between the shield 1070 and conductive structure 1080, or any combination thereof, may be selected to facilitate shielding from electromagnetic radiation in general or from RF energy having a particular frequency or frequencies or band(s) of frequencies.

FIG. 10B illustrates another embodiment of a shield 1070 that is disposed over a header 1050 of a control module 1002. The body 1014 of the control module includes a conductive structure 1080, such as an electrode. A discrete capacitor 1084b, or combination of capacitors in parallel or series or any combination thereof, is disposed between the shield 1070 and the conductive structure 1080 so that the shield and conductive structure are capacitively coupled. Any of the capacitance of the capacitor(s) 1084b, as well as the separation distance and extent of overlap between the shield 1070 and conductive structure 1080, or any combination thereof, may be selected to facilitate shielding from electromagnetic radiation in general or from RF energy having particular frequency or frequencies or band(s) of frequencies.

Conductively or capacitively coupling the shield to a conductive structure on the body of the control module may improve the efficiency of the shield to resist penetration of RF energy or reduce magnetic field gradient-induced heating or both. On the other hand, if the shield remains unconnected from any conductive structure on the body of the control module, the shield will not generally couple to the electrodes of the lead(s) which may also be desirable under some circumstances.

Figure 11A:
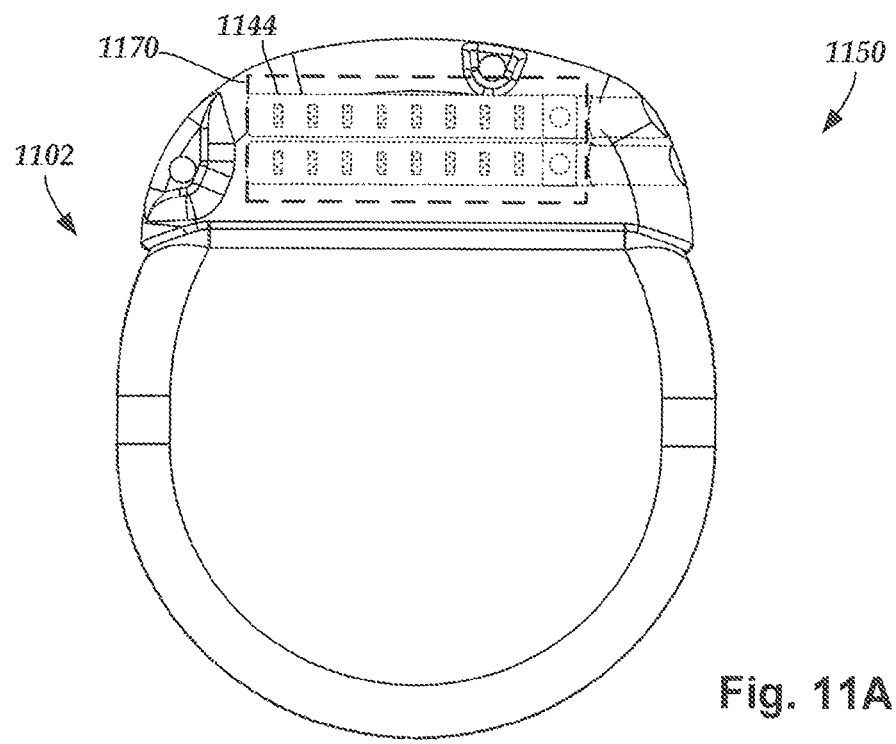
FIG. 11A is a schematic side view of one embodiment of a control module with a tube-shaped shield disposed within the header, according to the invention.
Figure 11B:
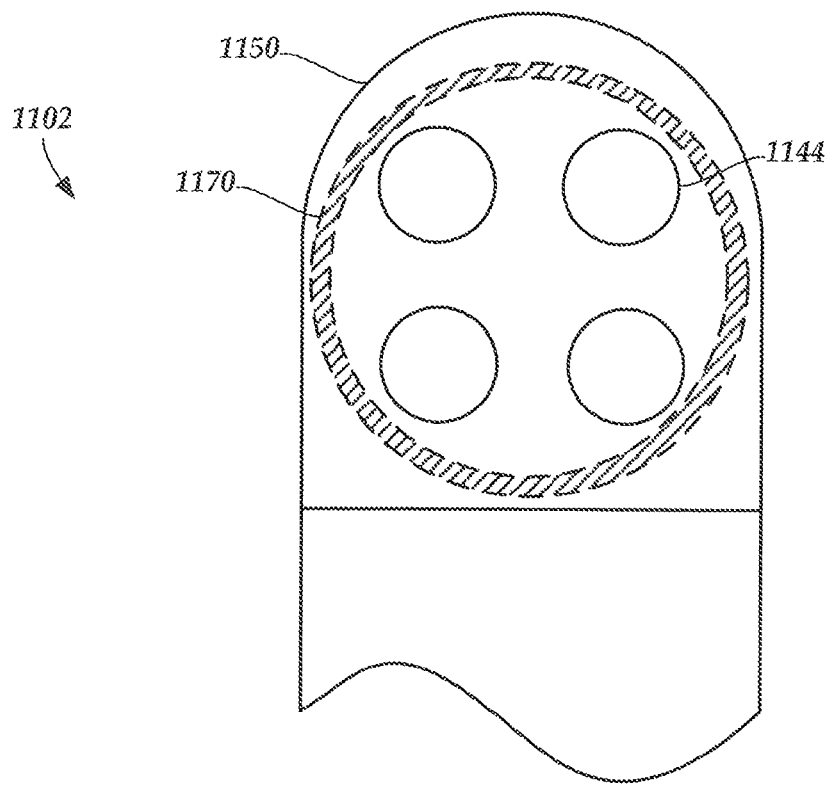
FIG. 11B is a schematic front view of a portion of the lead-receiving side of one embodiment of the control module of FIG. 11A with the tube-shaped shield, according to the invention.

In some embodiments, the shield is disposed within the header instead of over or on the header. FIGS. 11A and 11B illustrate one embodiment of a tube-shaped shield 1170 disposed within a header 1150 of a control module 1102 around one or more conductive assemblies 1144 that are arranged to each receive a proximal end of a lead or lead extension. Although the shield 1170 is illustrated with a circular cross-section, it will be recognized that shields with other cross-sections, such as square, rectangular, oval, triangular, octagonal, or hexagonal, can be used.

The shield 1170 is typically made of metal, alloy, or any other suitable conductive material. In at least some embodiments, the shield 1170 is a solid tube. In other embodiments, the shield 1170 is a mesh. Optionally, the shield 1170 may extend to either one end or both ends of the header 1150 to provide a tissue connection to the shield 1170 when the control module 1102 is implanted. This tissue connection may facilitate dissipation of currents induced in the shield.

Figure 12:
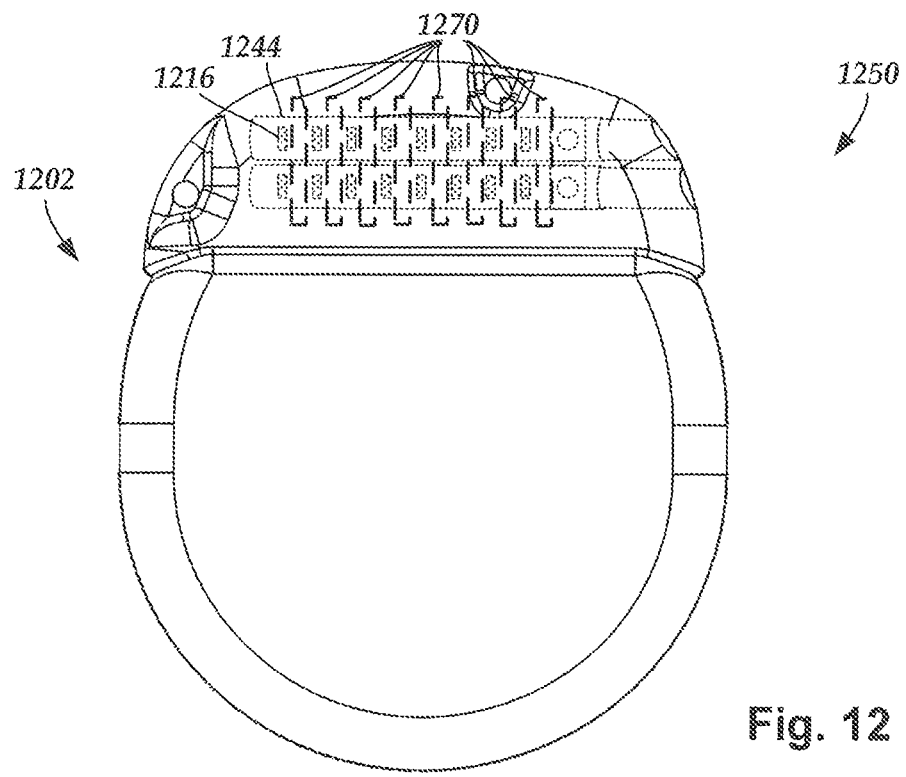
FIG. 12 is a schematic side view of one embodiment of a control module with a tube-shaped shield, formed in multiple parts, disposed within the header, according to the invention.

FIG. 12 illustrates another embodiment in which the shield 1270 is divided into several parts disposed between the contacts 1216 of the conductive assemblies 1244. When a lead or leads are inserted into the header, the shield 1270 is disposed over the portions of the leads with conductive wires which are the most likely to be adversely affected by RF irradiation. The conductive contacts on the lead and the contact 1216 of the control module will shield the lead to at least some extent.

The shield 1270 is typically made of metal, alloy, or any other suitable conductive material. In at least some embodiments, the shield 1270 is a solid tube. In other embodiments, the shield 1270 is a mesh.

It will be understood that shields 1170, 1270 can optionally be coupled conductively or capacitively to a conductive structure disposed on a surface of the body of the control module, as disclosed with respect to the embodiments illustrated in FIGS. 9, 10A, and 10B.

Figure 13:
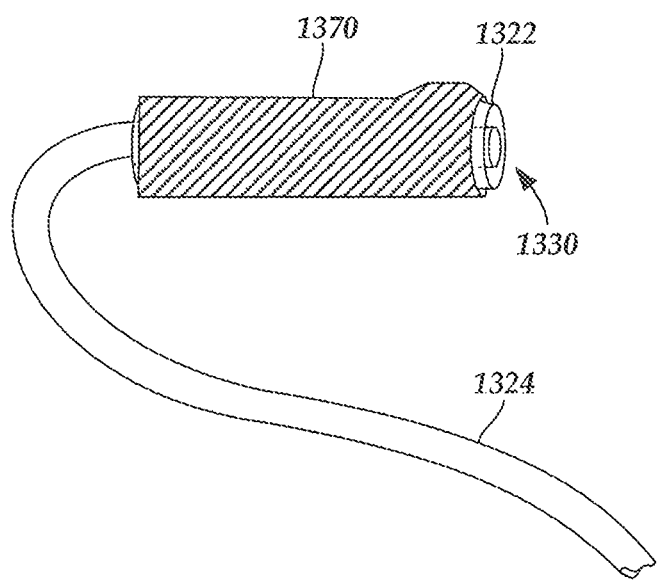
FIG. 13 is a schematic side view of one embodiment of a connector assembly of a lead extension with shield disposed around the connector assembly, according to the invention.

Alternatively or additionally, the shields described above can be adapted for use with a connector assembly of a lead extension or any other connector assembly of another component of the electrical stimulation system. FIG. 13 illustrates one embodiment of a lead extension 1324 having a connector assembly 1322 with a shield 1370 disposed over at least a portion of the connector assembly leaving the port 1330 open to receive one or more leads. The shield 1370 is conductive and can be similar in materials to any of the shield embodiments described above with respect to FIGS. 4-8. For example, the shield 1370 can be formed of a sheet, foil, mesh, or layer of conductive material disposed on the surface of the connector assembly 1322. The shield 1370 may include a window (not shown) for viewing at least a portion of the lead(s) inserted into the connector assembly 1322. The shield 1370 may have a frequency selective surface or a patterned arrangement with, for example, stripes or slats. The shield 1370 may be formed by doping or impregnating polymeric material of the connector assembly with conductive material.

Figure 14:
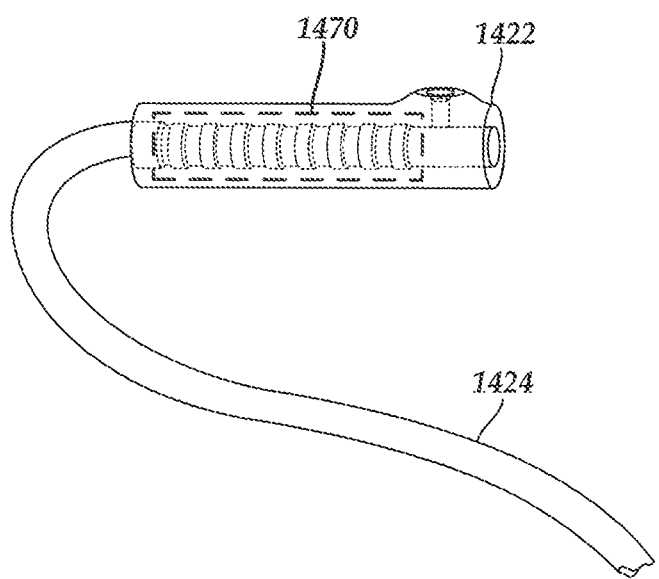
FIG. 14 is a schematic side view of one embodiment of a connector assembly of a lead extension with a tube-shaped shield disposed within the connector assembly, according to the invention.

FIG. 14 illustrates another embodiment of a shield 1470 for using with a lead extension 1424 having a connector assembly 1422. The shield 1470 is a tube-shaped element disposed within connector assembly 1422 and around at least a portion of the connector assembly 1422 that receives the lead(s). The shield 1370 is conductive and can be similar in materials to any of the shield embodiments described above with respect to FIGS. 11A-12. For example, the shield may be a single tube-shaped element or multiple tube-shaped elements spaced apart from each other.

Figure 15:
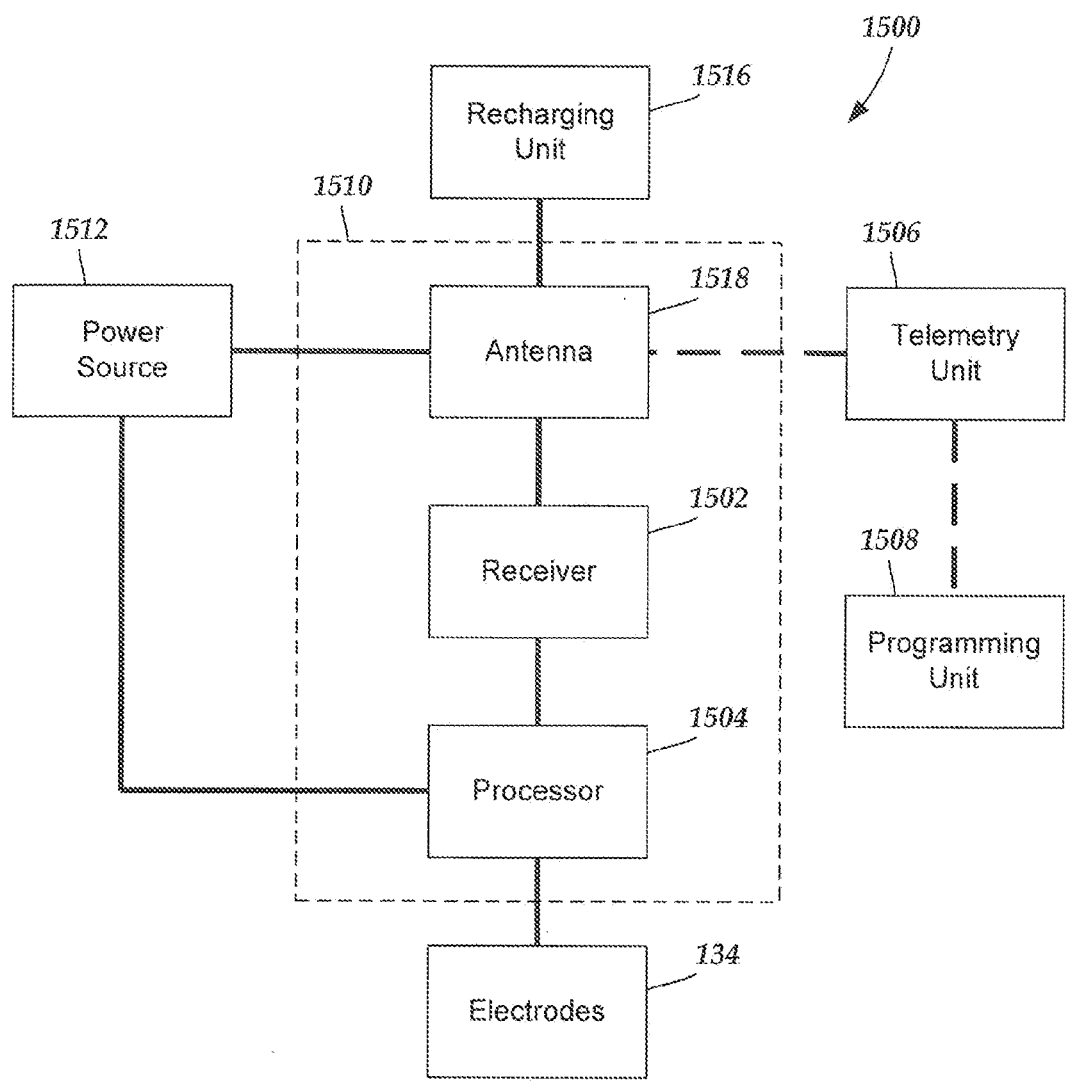
FIG. 15 is a schematic overview of one embodiment of components of a stimulation system, including an electronic subassembly disposed within a control module, according to the invention.

FIG. 15 is a schematic overview of one embodiment of components of an electrical stimulation system 1500 including an electronic subassembly 1510 disposed within a control module. It will be understood that the electrical stimulation system can include more, fewer, or different components and can have a variety of different configurations including those configurations disclosed in the stimulator references cited herein.

Some of the components (for example, power source 1512, antenna 1518, receiver 1502, and processor 1504) of the electrical stimulation system can be positioned on one or more circuit boards or similar carriers within a sealed housing of an implantable pulse generator, if desired. Any power source 1512 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 1518 or a secondary antenna. The external power source can be in a device that is mounted on the skin of the user or in a unit that is provided near the user on a permanent or periodic basis.

If the power source 1512 is a rechargeable battery, the battery may be recharged using the optional antenna 1518, if desired. Power can be provided to the battery for recharging by inductively coupling the battery through the antenna to a recharging unit 1516 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1504 is generally included to control the timing and electrical characteristics of the electrical stimulation system. For example, the processor 1504 can, if desired, control one or more of the timing, frequency, strength, duration, and waveform of the pulses. In addition, the processor 1504 can select which electrodes can be used to provide stimulation, if desired. In some embodiments, the processor 1504 may select which electrode(s) are cathodes and which electrode(s) are anodes. In some embodiments, the processor 1504 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1508 that, for example, allows modification of pulse characteristics. In the illustrated embodiment, the processor 1504 is coupled to a receiver 1502 which, in turn, is coupled to the optional antenna 1518. This allows the processor 1504 to receive instructions from an external source to, for example, direct the pulse characteristics and the selection of electrodes, if desired.

In one embodiment, the antenna 1518 is capable of receiving signals (e.g., RF signals) from an external telemetry unit 1506 which is programmed by a programming unit 1508. The programming unit 1508 can be external to, or part of, the telemetry unit 1506. The telemetry unit 1506 can be a device that is worn on the skin of the user or can be carried by the user and can have a form similar to a pager, cellular phone, or remote control, if desired. As another alternative, the telemetry unit 1506 may not be worn or carried by the user but may only be available at a home station or at a clinician's office. The programming unit 1508 can be any unit that can provide information to the telemetry unit 1506 for transmission to the electrical stimulation system 1500. The programming unit 1508 can be part of the telemetry unit 1506 or can provide signals or information to the telemetry unit 1506 via a wireless or wired connection. One example of a suitable programming unit is a computer operated by the user or clinician to send signals to the telemetry unit 1506.

The signals sent to the processor 1504 via the antenna 1518 and receiver 1502 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1500 to cease operation, to start operation, to start charging the battery, or to stop charging the battery. In other embodiments, the stimulation system does not include an antenna 1518 or receiver 1502 and the processor 1504 operates as programmed.

Optionally, the electrical stimulation system 1500 may include a transmitter (not shown) coupled to the processor 1504 and the antenna 1518 for transmitting signals back to the telemetry unit 1506 or another unit capable of receiving the signals. For example, the electrical stimulation system 1500 may transmit signals indicating whether the electrical stimulation system 1500 is operating properly or not or indicating when the battery needs to be charged or the level of charge remaining in the battery. The processor 1504 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable control module for an electrical stimulation system, the control module comprising:
    a sealed body;
    an electronic subassembly disposed in the sealed body and configured and arranged to generate electrical stimulation signals for delivery through a lead coupled to the implantable control module;
    a header coupled to the sealed body, the header comprising at least one connector assembly, each connector assembly defining a port with each connector assembly configured and arranged to receive a proximal portion of a lead inserted into the port, the header further comprising a plurality of contacts disposed within each connector assembly and configured and arranged to make contact with terminals disposed on a lead when the lead and terminals are received in the connector assembly and to electrically couple the terminals of the lead to the electronic subassembly; and
    a conductive shield disposed over at least a portion of the at least one connector assembly of the header, wherein the conductive shield is configured and arranged to hinder generation of current in the header or in a portion of a lead received in the header in response to application of an external radiofrequency (RF) or magnetic field, wherein the conductive shield comprises a substrate and a plurality of conductive stripes or conductive slats disposed on the substrate and arranged parallel to the at least one connector assembly, wherein the conductive shield is disposed over at least a portion of the header.

2. The control module of claim 1, further comprising a conductive structure disposed on the sealed body and electrically coupled to the electronic subassembly.

3. The control module of claim 2, wherein the conductive shield is conductively coupled to the conductive structure.

4. The control module of claim 1, wherein the conductive shield comprises at least a portion of the header that is formed of a polymer doped or impregnated with conductive particles to make the portion of the header conductive.

5. The control module of claim 1, wherein the conductive shield comprises a frequency selective surface formed on a portion of the header or on a substrate that is disposed over at least a portion of the header.

6. An electrical stimulation system, comprising:
    the control module of claim 1; and
    a lead coupleable to the control module, the lead comprising a plurality of electrodes configured and arranged to deliver stimulation signals generated by the control module to patient tissue.

7. An implantable lead extension for an electrical stimulation system, the lead extension comprising:
    an extension body having a proximal end, a distal end, and a longitudinal length;
    a plurality of conductive contacts disposed along the proximal end of the extension body;
    a connector assembly disposed on the distal end of the extension body, the connector assembly defining at least one port configured and arranged to receive a proximal portion of a lead inserted into the port, the connector assembly further comprising a plurality of contacts disposed within the connector assembly and configured and arranged to make contact with terminals disposed on a lead when the lead and terminals are received in the connector assembly;

a plurality of conductive wires electrically coupling the conductive contacts along the proximal end of the extension body to the contacts of the connector assembly; and a conductive shield disposed over at least a portion of the connector assembly, wherein the conductive shield is configured and arranged to hinder generation of current in the connector assembly or in a portion of a lead received in the connector assembly in response to application of an external radiofrequency (RF) or magnetic field, wherein the conductive shield comprises a substrate and a plurality of conductive stripes or conductive slats disposed on the substrate and arranged parallel to the connector assembly, wherein the conductive shield is disposed over at least a portion of the connector assembly.

8. The lead extension of claim 7, wherein the conductive shield defines at least one window in the conductive shield configured and arranged to allow viewing of a portion of the connector assembly.

9. The lead extension of claim 7, wherein the conductive shield comprises a frequency selective surface formed on a portion of the connector assembly or on a substrate that is disposed over at least a portion of the connector assembly.

10. An electrical stimulation system, comprising:
the lead extension of claim 7; and
a lead coupleable to the lead extension, the lead comprising a plurality of electrodes.

11. An implantable lead extension for an electrical stimulation system, the lead extension comprising:

an extension body having a proximal end, a distal end, and a longitudinal length;

a plurality of conductive contacts disposed along the proximal end of the extension body;

a connector assembly disposed on the distal end of the extension body, the connector assembly defining an exterior surface and at least one port configured and arranged to receive a proximal portion of a lead inserted into the port, the connector assembly further comprising a plurality of contacts disposed within the connector assembly and configured and arranged to make contact with terminals disposed on a lead when the lead and terminals are received in the connector assembly;

a plurality of conductive wires electrically coupling the conductive contacts along the proximal end of the extension body to the contacts of the connector assembly; and a conductive shield disposed over at least a portion of the exterior surface of the connector assembly. wherein the conductive shield is configured and arranged to hinder generation of current in the connector assembly or in a portion of a lead received in the connector assembly in response to application of an external radiofrequency (RF) or magnetic field, wherein the conductive shield comprises a tube-shaped shield disposed within the connector assembly and around at least a portion of the connector assembly.

12. An electrical stimulation system, comprising:
the lead extension of claim 11; and
a lead coupleable to the lead extension, the lead comprising a plurality if electrodes.

\* \* \* \* \*